United States Patent
Bergeron, Jr.

(10) Patent No.: US 6,242,492 B1
(45) Date of Patent: Jun. 5, 2001

(54) N,N'-BIS(2-HYDROXYBENZYL) ETHYLENEDIAMINE-N,N'-DIACETIC ACID IN IRON CHELATING THERAPY

(76) Inventor: Raymond J. Bergeron, Jr., 6220 NW. 56$^{th}$ La., Gainesville, FL (US) 32653

( * ) Notice: Subject to any disclaimer, the term of this patent is extended or adjusted under 35 U.S.C. 154(b) by 0 days.

(21) Appl. No.: 09/467,943

(22) Filed: Dec. 21, 1999

Related U.S. Application Data

(63) Continuation-in-part of application No. PCT/US99/02388, filed on Feb. 3, 1999.
(60) Provisional application No. 60/073,603, filed on Feb. 4, 1998.

(51) Int. Cl.$^7$ ..................... A61K 31/195; C07C 229/00
(52) U.S. Cl. ............................................. 514/566; 562/451
(58) Field of Search .............................. 514/566; 562/451

(56) References Cited

U.S. PATENT DOCUMENTS

| | | |
|---|---|---|
| 3,005,848 | 10/1961 | Knell et al. . |
| 3,758,540 | 9/1973 | Martell . |
| 3,833,590 | 9/1974 | Dazzi . |
| 4,116,991 | 9/1978 | Leneuf . |
| 4,130,582 | 12/1978 | Petree et al. . |
| 4,352,751 | 10/1982 | Wieder et al. . |
| 4,454,106 | 6/1984 | Gansow et al. . |
| 4,528,196 | 7/1985 | Pitt . |
| 4,647,447 | 3/1987 | Gries et al. . |
| 4,909,257 | 3/1990 | Engelstad et al. . |
| 5,057,302 | 10/1991 | Johnson et al. . |
| 5,227,474 | 7/1993 | Johnson et al. . |
| 5,534,241 | 7/1996 | Torchilin et al. . |

FOREIGN PATENT DOCUMENTS

| | | |
|---|---|---|
| WO 95/16663 | 6/1995 | (WO) . |
| WO 97/36885 | 10/1997 | (WO) . |
| WO 97/44313 | 11/1997 | (WO) . |

OTHER PUBLICATIONS

Bergeron et al., "HBED: The Continuing Development of a Potential Alternative to Deferoxamine for Iron–Chelating Therapy," *Blood*, 93(1):370–375 (1999).
Bergeron et al., "HBED: A Potential Alternative to Deferoxamine for Iron–Chelating Therapy," *Blood* 91(4):1445–1452 (1998).
Brittenham, "Development of Iron–Chelating Agents for Clinical Use," *Blood*, 80(3):569–574 (1992).
Grady et al., "HBED: A Potential Oral Iron Chelator," *Sixth Cooley's Anemia Symposium*, Annals of the New York Academy of Sciences, vol. 612:361–368 (1990).
Grady et al., "Results from a Phase I Clinical Trial of HBED," *Progress in Iron Research*, Edited by Hershko et al., Plenum Press, New York (1994).
Hider et al., "Clinically Useful Chelators of Tripositive Elements," *Progress in Medicinal Chemistry*, Edited by Ellis et al., 28:41–173, Elsevier Science Publishers, B.V. (1991).
Hunt, "Phenolic Aminocarboxylic Acids as Gallium–Binding Radiopharmaceuticals," *Nucl. Med.*, 23:123–125 (1984).
Kim et al., "Effectiveness of Oral Iron Chelators Assayed in the Rat," *Am. J. Hematology*, 24:277–284 (1987).
L'Eplattenier et al., "New Multidentate Ligands. VI. Chelating Tendencies of N,N'–Di(2–hydroxybenzyl)ethylenediamine–N,N'–diacetic Acid," *J. Am. Chemical Society*, 89:837–843 (1967).
Peter et al., "A Comparative Evaluation of Iron Chelators in a Primate Model," *The Development of Iron Chelators for Clinical Use*, 17:374–394, CRC Press (1994).
Pitt et al., "Esters and Lactones of Phenolic Amino Carboxylic Acids: Prodrugs for Iron Chelation," *J. Med. Chem.*, 29:1231–1237 (1986).
Porter, "Oral Iron Chelators: Prospects for Future Development," *Eur. J. Haematol.*, 43:271–285, 1989.
Rajan et al., "Studies on the Chelation of Aluminum for Neurobiological Application," *J. Inorganic Biochem.*, 14:339–350 (1981).
Schnelbi et al., "Toward Better Chelation Therapy: Current Concepts and Research Strategy," *The Development of Iron Chelators for Clinical Use*, 7:132–149, CRC Press (1994).
Smith, "Iron Excretion in Thalassaemia Major After Administration of Chelating Agents," *British Medical J.*, pp. 1577–1580, Dec. 15, 1962.
Taliaferro et al., "New Multidentate Ligands. 22. N,N'–Dipyridoxyethylenediamine–N,N'–diacetic Acid: A New Challenging Ligand for Trivalent Metal Ions," *Inorg. Chem.*, 23:1188–1192 (1984).

*Primary Examiner*—James H. Reamer
(74) *Attorney, Agent, or Firm*—Cooley Godward LLP

(57) ABSTRACT

The use of a novel mono-cationic salt of N,N'-bis(2-hydroxybenzyl)ethylenediamine-N,N'-diacetic acid (HBED) in iron chelating therapy is disclosed. In particular, the invention relates to the subcutaneous use of a mono cationic salt of HBED for treating a human with a disease treatable by an iron chelator such as iron overload, especially transfusional iron overload.

39 Claims, No Drawings

N,N'-BIS(2-HYDROXYBENZYL) ETHYLENEDIAMINE-N,N'-DIACETIC ACID IN IRON CHELATING THERAPY

CROSS REFERENCE

This patent application is a continuation-in-part of PCT Application No. PCT/US99/02388 filed Feb. 3, 1999, which in turn is a continuation-in-part of U.S. provisional application Ser. No. 60/073,603 filed Feb. 4, 1998. Each of these cited applications are hereby incorporated, in their entirety, by reference.

ACKNOWLEDGEMENTS

This invention was supported in part by a grant from the National Institutes of Health, No. DK49108. The U.S. Government may have rights in this invention.

INTRODUCTION

TECHNICAL FIELD

This invention relates to the use of a mono-cationic salt of N,N'-bis(2-hydroxybenzyl) ethylenediamine-N,N'-diacetic acid (HBED) e.g. the mono-sodium salt, in iron chelation therapy. In particular, the invention relates to the subcutaneous use of a mono-cationic salt of HBED for treating a primate, in particular a human, that is afflicted with a condition treatable with an iron chelating agent, e.g., iron overload, especially transfusional iron overload.

BACKGROUND

In humans and other primates iron is stored in the body in the form of ferritin and hemosiderin, which are protein complexes, and is transported in the plasma via another protein complex, namely transferrin. The manner in which iron is utilized is very efficient, but there is no specific mechanism that exists for the elimination of excess iron. Under conditions of iron overload the protein complexes become saturated with iron, resulting in excess iron being deposited in tissues which induces iron toxicity, and ultimately leads to peroxidative tissue damage. An iron overload condition may occur for example through a genetically determined error that results in increased absorption of iron from a normal diet or may occur through repeated blood transfusions to treat a condition, e.g., sickle-cell anemia or Cooley's anemia.

One way of treating iron overload is by administering an iron chelator. In principle, the chelator transforms the deposited iron back into a soluble form that is then capable of excretion. However, none of the available iron chelators employed for this purpose is ideal; the chelators have poor gastrointestinal absorption, or have low efficacy and/or undesirable side effects.

One iron chelator that overcomes some of these disadvantages, and is widely used in therapy, is deferoxamine B (DFO) as the methanesulfonate salt, also known as desferrioxamine B mesylate (DFOM). This is available commercially as Desferal from Novartis (previously Ciba-Giegy). In general DFOM is capable of controlling excess body iron and can prolong survival and prevent or ameliorate organ dysfunction in a person suffering from iron overload. However, DFOM is far from an ideal treatment for iron overload. It is cumbersome, inefficient, expensive, and unpleasant to the patient. Because DFOM is poorly absorbed from the gastrointestinal tract and rapidly eliminated from circulation, prolonged parenteral infusion is required for treatment; it is generally administered by a portable infusion pump for 9–12 hours daily. Not surprisingly, very few patients are capable of complying with such a demanding regimen. Additionally, DFOM is very inefficient as an iron chelator, in that typically 5% or less of the compound administered binds iron.

Yet another disadvantage is the cost of DFO, which is commercially produced by large scale fermentation of a strain of *Streptomyces pilosus*, a method of manufacture that is very expensive. In addition, almost all patients experience an allergic reaction to DFOM, which is uncomfortable and sometimes very painful. The allergic reaction is thought to be caused by cytokines and/or other fermentation products formed during the fermentation process that are not completely removed during purification of the crude product mixture.

It would therefore be desirable to provide a method for treating iron overload that employs a safe and inexpensive alternative to DFOM. Ideally, the iron chelator would not be associated with an allergic reaction in patients, and would be a more efficient chelator of iron than DFOM.

HBED is a compound known to be an iron chelator. U.S. Pat. No. 3,758,540 discloses that iron chelates of HBED and other compounds are useful as a source of iron in plant nutrition. See also U.S. Pat. No. 4,116,991. U.S. Pat. No. 4,528,196 discloses, on the basis of testing in rat and mouse screens, that HBED and its alkyl esters are orally active in the treatment of iron overload, and more active given orally than DFO given intraperitoneally. However, the rodent findings were not substantiated in higher animals. Testing in the *Cebus apella* monkey screen, which is known to be an excellent predictor of the behavior of chelators in humans, showed that DFOM administered subcutaneously has significantly higher activity than HBED or its dimethyl ester given orally (Bergeron et al., Blood, 81:2166 (1993), Peter et al., "A Comparative Evaluation of Iron Chelators in a Primate Model", pp 373, Development of Iron Chelators for Clinical Use, Boca Raton, CRC Press (1994)). It has also been demonstrated that HBED, when given orally to human patients, provides iron excretion at a level that is ineffective for the treatment of iron overload (Grady et al., "Preliminary Results from a Phase I Clinical Trial of HBED", in the Development of Iron Chelators for Clinical Use, Boca Raton, CRC Press (I 994), pp 395).

It was therefore totally unexpected, based upon the above findings, that mono-cationic salts of HBED would prove to be highly efficient compounds for treating iron overload when administered subcutaneously. These HBED salts upon subcutaneous administration do not require prolonged parenteral infusion for effective iron chelation and excretion, are not associated with an allergic reaction in primates, and are a more efficient chelators of iron than DFOM.

OBJECTS OF THE INVENTION

An object of this invention is to provide an improved method for treating a condition in primates, particularly humans, which condition is treatable by an iron chelator.

It is a further object of this invention to provide a composition for the subcutaneous treatment of a condition that is treatable by an iron chelator, particularly where the condition is iron overload.

It is a further object of this invention to provide a process for making a subcutaneously administratable composition useful for treating a condition treatable with an iron chelator, particularly where the condition is iron overload.

It is a further object of this invention to provide an improved method and composition for treatment of a condition treatable with an iron chelator, which method and composition do not require treatment of a patient by prolonged infusion.

It is a further object of this invention to provide a treatment method and composition that minimizes allergic reactions to patients being treated for a condition treatable by an iron chelator.

Other objects of the invention may be apparent to one of skill in the art upon reading the following specification and claims.

SUMMARY OF THE INVENTION

One aspect of the present invention relates to a method of treatment of a primate having a condition that is treatable by an iron chelator. The method comprises subcutaneously administering a therapeutically effective amount of a mono-cationic salt of N,N'-bis(2-hydroxybenzyl)ethylenediamine-N,N'-diacetic acid (HBED), which is represented by formula (I), wherein M is a monovalent, pharmaceutically acceptable cation as defined below.

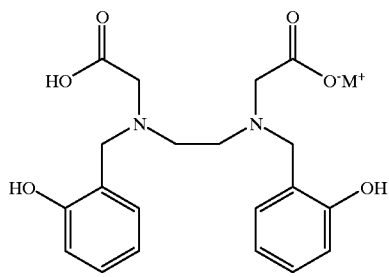

(I)

The method is particularly suitable for treating iron overload in a primate, particularly a human.

Another aspect of the invention is a compound represented by formula (1), ie. a mono-cationic salt of HBED. The mono-sodium or the mono-ammonium salts of HBED are preferred.

Another aspect of this invention is a pharmaceutical composition comprising a pharmaceutically-acceptable excipient suitable for subcutaneous injection in combination with a mono-cationic salt of HBED.

Still another aspect of this invention is an article of manufacture that comprises a container containing a pharmaceutical composition comprising a mono-cationic salt of HBED, wherein the container holds a therapeutically effective amount of the mono-cationic salt of HBED and is associated with printed labelling instructions for subcutaneous administration of the composition to treat a condition that is treatable by an iron chelator.

Still another aspect of this invention is a process for preparing a pharmaceutical composition, which process comprises combining a pharmaceutically-acceptable excipient suitable for subcutaneous injection with a mono-cationic salt of HBED.

Other aspects may become apparent upon further reading of this patent application.

DESCRIPTION OF PRESENTLY PREFERRED EMBODIMENTS

Method of Treatment

One aspect of this invention is a method of treating a primate that has a condition that is treatable by an iron chelator. The method comprises the subcutaneous administration of a therapeutically-effective amount of a monocationic salt of HBED. A condition treatable by an iron chelator includes any disease of an individual primate, particularly a human, in which the individual shows improvement when an iron chelator is administered. A condition treatable by an iron chelator may occur, e.g., through a genetically determined error that results in increased absorption of iron from a normal diet or may occur through repeated blood transfusions to treat a condition. Such conditions in which iron chelators may be used include malaria, cancer, HIV infections, inflammatory bowel disease, host v. graft rejection, graft v. host rejection, reperfusion injury, neurological disorders, and iron overload. The condition in which this method is most useful is "iron overload." It is characterized by greater than normal focal or generalized deposition of iron within body tissues.

When such focal or generalized deposition is associated with tissue injury, with total body iron greater than about 15 grams, it is known as hemochromatosis, which may be primary or secondary. Primary hemochromatosis most commonly arises from an autosomal recessive trait linked to the histocompatibility locus on chromosome 6p that results in increased absorption of iron from a normal diet. This form of primary hemochromatosis affects 3 to 8 people per thousand. Primary hemochromatosis may also occur as a result of other genetically determined errors including conditions identified as atransferrinemia, thalassemia major, and y-linked hypochromic anemia. While the Merck Manual, 15th Edition, sets forth the classification of these conditions, differential diagnosis is difficult. Diagnosis will depend on the history of iron administration, the examination of relatives of the patient, the degree of iron overload, and the presence or absence of localizing signs.

Hemochromatosis rarely occurs before middle age. Typical manifestations are cirrhosis of the liver, brown pigmentation of the skin, diabetes mellitus, and cardiomyopathy, which may be manifested by cardiomegaly, congestive failure, and arrhythmias or conduction disturbances. In the case of pituitary failure, testicle atrophy and loss of libido may be seen. Abdominal pain, arthritis and chondrocalcinosis occur less often. Focal hemosiderosis (the accumulation of hemosiderin in tissues) chiefly occurs in the lungs and kidneys. Pulmonary hemosiderosis may be due to recurrent pulmonary hemorrhage which occurs as an idiopathic entity, e.g., as part of Goodpasture's Syndrome.

Diagnosis of the above mentioned conditions may be found in Merck's Manual. Each of these conditions should be considered as a condition that is treatable by an iron chelator.

Secondary hemochromatosis or hemosiderosis may result from increased parenteral iron intake such as through repeated transfusion (transfusional iron overload). Repeated transfusions are often required for various diseases, such as, for example, sickle-cell anemia, thalassemia, Cooley's anemia, and myelodysplasia. The use of a monocationic salt of HBED to prevent iron overload in chronic transfusion therapy is especially important in the treatment of young children with sickle cell anemia. Secondary hemochromatosis or hemosiderosis may also be caused by iron dextran taken intramuscularly, increased iron absorption due to increased iron ingestion, or may be due to anemia with erythroid hyperplasia, or may possibly be linked to megadoses of Vitamin C. Focal hemosiderosis may be pulmonary, renal, or hepatic.

The term "treatment" as used herein covers any treatment of a condition treatable by an iron chelator in a primate, particularly a human, and includes:

(i) preventing the condition from occurring in a subject which may be predisposed to the condition but has not yet been diagnosed as having it;

(ii) inhibiting the condition, e.g., arresting or slowing its development; or (iii) relieving the condition, e.g., causing regression of the condition.

The method of administration that has been found to be surprisingly effective is the subcutaneous administration of mono-cationic salt of HBED. By subcutaneous administration it is meant that the drug in the form of an appropriate injectable composition is injected into the areola connective tissue just below the skin. The injection may be a formulation, particularly a solution, that provides a controlled release of the active entity, but is preferably an aqueous solution. Generally, the subcutaneous administration will be done with excipients that are suitable for subcutaneous administration, which means that the excipients will have to meet USP considerations in being appropriate for injectable compositions. Thus, the composition will need to be sterile to avoid any complications due to insterility at the injection site.

The amount of the mono-cationic salt that will be present in the composition to be injected and that will be injected is a therapeutically-effective amount, that is, an amount which is sufficient to result in successful treatment as defined above when administered to a primate exhibiting a condition treatable by an iron chelator, e.g., a condition of iron overload. The therapeutically effective amount will vary depending on the subject and condition being treated, the severity of the affliction and the manner of administration, and may be determined routinely by one of ordinary skill in the art in light of the disclosure of this specification. The typical daily dose varies according to individual needs, the severity of the condition to be treated, and the specific salt. Generally, about 5 micromoles ($\mu$moles) to about 500 $\mu$moles of the active moiety i.e., HBED, will be administered to a patient on a per kilogram (Kg) basis. Suitable doses are in the general range from about 1 to about 200 mg/Kg body weight of the recipient per day, preferably in the range from about 5 to about 100 mg/Kg, most preferably in the range from about 10 to about 80 mg/Kg as the active moiety (HBED).

Novel Compounds

As mentioned hereinbefore, the key to the treatment is the subcutaneous administration of the mono-cationic salt of HBED as shown in Formula I hereinbefore. The unique characteristics of the mono-cationic salts that make them ideal for subcutaneous administration are their high water-solubility and the fact that the pH of the resulting solution is in a range that is generally nonirritating, ie., about 7.0–8.0, for subcutaneous injection. "Mono-cationic salt of HBED" means a salt that retains the biological effectiveness and properties of HBED (i.e., the iron chelation ability), and that is not biologically or otherwise undesirable. The salt is free of other impurities and ionizes when dissolved in water. The salt may be associated with water in its crystalline form or may be free of water.

Mono-cationic salts may be prepared from inorganic and organic bases or other methods known in the art. Salts derived from inorganic bases include, but are not limited to, the sodium, potassium, lithium and ammonium salts. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, N-alkylglucamines, theobromine, purines, piperidine, N-ethylpiperidine, and tetra-n-butylammonium hydroxide.

Preferred are the monosodium salt and the monoammonium salt.

A mono-cationic salt is readily prepared by reacting an organic or inorganic base with HBED in a 1:1 molar ratio. Generally the reaction is carried out in a suitable solvent under cooling conditions because the reaction is exothermic, ie. an acid/base reaction. Usually a suitable solvent is water with the reaction temperature being kept below about 40° C. through cooling. Other methods may be apparent to one of ordinary skill in the art.

The following reaction sequence sets forth an exemplary method. In the reaction sequence M represents a monovalent cation.

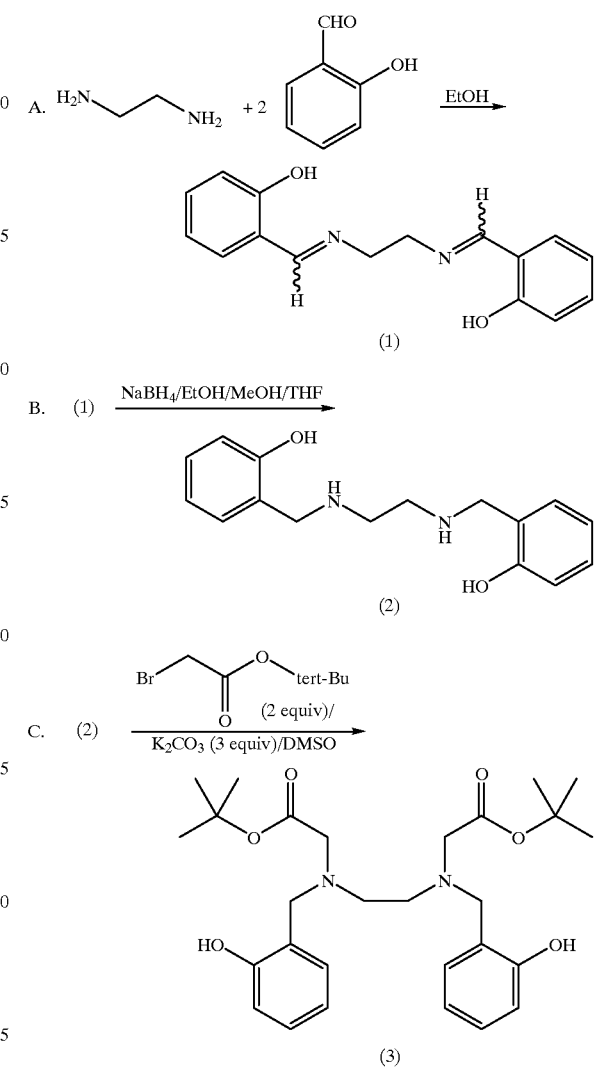

D. (3) $\xrightarrow{\text{HCOOH}}$

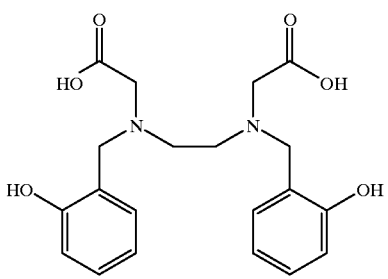

(4)

E. (4) $\xrightarrow{\text{MOH (1 equiv)}}$

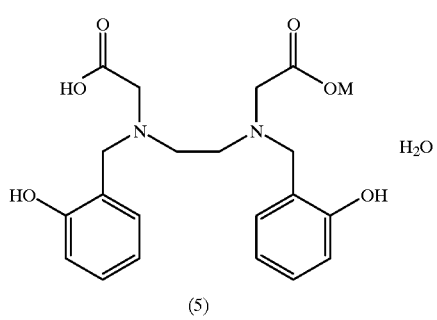

$H_2O$ (5)

The monovalent, mono-cationic salt of HBED can be prepared from multi (monovalent) cationic salts of HBED (disodium HBED for example) or from anionic salts of HBED (HBED hydrocholoride for example) by appropriately adjusting the pH with an appropriate acid or base. However, in the process of pH adjustment, additional salts (NaCl for example) are produced, which unnecessarily raise the ionic strength of the product, usually to an undesirable level. Nonetheless, if the ionic strength can be lowered, or if in the particular formulation it can be accounted for and still result in an acceptable product, such pH adjustments can be used.

Pharmaceutical Compositions of the Invention

Broadly, the composition of the invention is the combination of a mono-cationic salt of HBED with a pharmaceutical excipient that is suitable for injection. Generally, the compositions of the invention may fall into one of three categories:

1. a solution that is ready for injection, 2. a dry soluble composition that is ready to be combined with a solvent just prior to use, i.e., a reconstitutable composition, or 3. a liquid concentrate ready for dilution prior to administration.

In preparing a composition for subcutaneous administration strict attention must be paid to tonicity adjustment to reduce irritation.

A reconstitutable composition is a sterile solid packaged in a dry form. A reconstitutable composition is preferred because it is more stable when stored as a dry solid rather than in a solution ready for immediate administration. The reconstitutable mono-cationic salts of HBED dissolve rapidly, e.g. in one minute or less. The dry solid is usually packaged in a sterile container with a butyl rubber closure to ensure the solid is kept at an optimal moisture range. A reconstitutable dry solid is formed by dry fill, spray drying, or freeze drying methods. Descriptions of these methods may be found in Pharmaceutical Dosage Forms: Parenteral Medications, Vol. 1, pps. 215–227.

The subcutaneous injections are generally dilute, and the component present in the higher proportion is the vehicle. The vehicle normally has no therapeutic activity and is nontoxic, but presents the active constituent to the body tissues in a form appropriate for absorption. Absorption normally will occur most rapidly and completely when the mono-cationic salt is presented as an aqueous solution. However, modification of the vehicle with water-miscible liquids or substitution with water-immiscible liquids can affect the rate of absorption. Preferably, the vehicle of greatest value for this subcutaneous composition is water that meets the USP specification for water for injection. Generally, water of suitable quality for compounding will either be prepared by distillation or reverse osmosis to meet these USP specifications. The appropriate specifications are spelled out in *Remington: The Science and Practice of Pharmacy* 19th Ed. at pps. 1526–1528. In preparing the compositions which are suitable for subcutaneous injection, one can use aqueous vehicles, water-miscible vehicles, and nonaqueous vehicles. Certain aqueous vehicles are recognized officially because of their valid use in parenterals generally, and subcutaneous injectables specifically.

Water-miscible vehicles are also useful in the formulation of the subcutaneous composition of this invention. These solvents are used primarily to affect the solubility of the various salts of the HBED. The most important solvents in this group are ethyl alcohol, polyethylene glycol, and propylene glycol.

Additional substances may be included in the subcutaneous injectable compositions of this invention to improve or safeguard the quality of the composition. Thus, an added substance may affect solubility, provide for patient comfort, enhance the chemical stability, or protect preparation against the growth of microorganisms. Thus, the composition may include an appropriate solubilizer, substances to act as antioxidants, and substances that act as a preservative to prevent the growth of microorganisms. These substances will be present in an amount that is appropriate for their function, but will not adversely affect the action of the composition as a treatment for iron overload. Examples of appropriate antimicrobial agents include thimerosal, benzethonium chloride, benzalkonium chloride, phenol, methyl p-hydroxybenzoate, and propyl p-hydroxybenzoate. Appropriate antioxidants may be found in *Remington* at p. 1529.

Generally the sterile, subcutaneously injectable composition of this invention will comprise about 0.01% by wt. to about 50% by wt. of mono-cationic salt, with the remainder being the appropriate excipient or excipients.

Method of Preparation

Another aspect of this invention flows from the discovery of the unusual results obtained by subcutaneous administration of the drug. This aspect is a method of preparing a pharmaceutical composition suitable for subcutaneous administration which process comprises combining the mono-cationic salt with a pharmaceutical excipient suitable for subcutaneous administration under conditions that are effective in providing a sterile composition suitable for subcutaneous administration. Thus, in preparing the compositions of this invention, care must be taken to ensure the final composition is sterile and suitable for subcutaneous injection. The process will generally follow currently approved good manufacturing procedures (GMP) in order to result in the desired subcutaneous product. When employing aqueous vehicles the USP water for injection must be used for preparing the composition itself and preferably is used in preparing the equipment for preparing the composition. The general considerations for preparing subcutaneous preparations may be found in *Remington: The Science and Practice of Pharmacy,* 19th Ed. Chap. 87.

Article of Manufacture

Another aspect of this invention is an article of manufacture that comprises a container holding a composition which is suitable for injection or reconstitution for injection in combination with printed labelling instructions providing a discussion of how to administer the composition subcutaneously. The composition will be contained in any suitable container that will not significantly interact with the composition and will be labelled with the appropriate labelling that indicates it will be for subcutaneous use. Associated with the container will be the labelling instructions consistent with the method of treatment as described hereinbefore. The container which holds the composition of this invention may be a container having a liquid composition suitable for injection which has an appropriate needle for injection and a syringe so that the patient, doctor, nurse, or other practitioner can administer the drug. Representative examples of a suitable container include those used with the Wyeth-Ayerst TUBEX® closed injection system, with the Smith-Kline Beecham injectable product COMPRAZINE®, and with the Hoechst-Rousell injectable product LASIX® pre-filled syringe. Alternatively, the composition may be a dry composition containing a soluble version of the monocationic salt of HBED, to be combined with an aqueous or nonaqueous vehicle to dissolve or suspend the composition. Alternatively, the container may have a suspension in a liquid or may be an insoluble version of the salt for combination with a vehicle in which the insoluble version will be suspended. Appropriate containers are discussed in *Remington*: Chapter 37.

The following examples are given as nonlimiting representations of various aspects of the invention to enable one of ordinary skill in the art to make and use the invention.

EXAMPLES

Starting Materials

Deferoxamine B in the form of the methanesulfonate salt (DFOM trade name: DESFERAL) was manufactured by Novartis Corp, previously Ciba-Geigy Ltd. (Basel, Switzerland). HBED monohydrochloride monohydrate was obtained from Strem Chemical Co (Newburyport, Mass.). Cremophor RH-40 was obtained from BASF (Parsippany, N.J.). *Cebus apella* monkeys were obtained from World Wide Primates (Miami, Fla.). All reagents and standard iron solutions were obtained from Aldrich Chemical Co. (Milwaukee, Wis.).

Example 1

This example explains how to handle *Cebus apella* monkeys for testing to determine the effectiveness of the method and composition of this invention.

A. Iron loading of *Cebus apella* monkeys

After intramuscular anesthesia with ketamine, an intravenous infusion was started in a leg vein. Iron dextran was added to approximately 90 mL of sterile normal saline and administered to the animals by slow infusion at a dose of 200 to 300 mg iron per Kg body weight over 45 to 60 minutes. Two to three infusions, separated by between 10 and 14 days, were necessary to provide about 500 mg iron per Kg body weight. After administration of iron dextran, the serum transferrin iron saturation rose to 70–80%. The serum half-life of iron dextran in humans is 2.5 to 3.0 days. At least twenty half-lives, sixty days, passed before using any of the animals in experiments evaluating iron-chelating agents.

B. Iron-balance studies in *Cebus apella* monkeys

Seven days before the administration of the drug, the animals were placed in metabolic cages and started on a low-iron liquid diet. The monkeys were maintained on the low-iron liquid diet for the duration of the experiment. They were given food according to their body weight, and intake was very carefully monitored.

Three days prior to drug administration, day −2 to day 0, baseline iron intake and output values were measured. This same measurement was made for day +1 to day +3. The total amount of iron intake was compared with the total amount of iron excreted.

C. Primate fecal and urine samples

Fecal and urine samples were collected at 24 hour intervals. The collections began four days prior to the administration of the test drug and continued for an additional five days after the drug was given. Fecal samples were assayed for the presence of occult blood, weighed, and mixed with distilled deionized water prior to autoclaving for 30 minutes. The mixture was then freeze-dried, and a known portion of the powder was mixed with low-iron nitric acid and refluxed for 24 hours. Once any particulate matter in the digested samples was removed by centrifugation, iron concentrations were determined by flame atomic absorption. Monkey urine samples were acidified and reconstituted to initial volume after sterilization, if necessary.

Example 2

This example explains how to prepare a formulation for s.c. administration and to compare to a method for oral administration.

Drug preparation and administration

In the primates, DFOM was administered s.c. in sterile water for injection at a dose of 150 $\mu$moles/Kg, while HBED was first dissolved in a phosphate buffer, ph 7.4, thus forming the mono-sodium salt and given s.c. in 40% wt./vol. Cremophor RH-40 at a dose of 75 or 150 $\mu$moles/Kg. In addition, in order to more closely mimic clinical applications in patients, mono-sodium HBED was also given to the monkeys s.c. at a dose of 150 $\mu$moles/Kg in a phosphate buffer; no Cremophor vehicle was used.

Calculation of iron chelator efficiency

The efficiency of each chelator was calculated on the basis of a 1:1 ligand-iron complex. In the monkeys, the numbers were generated by averaging the iron output for four days prior to the administration of the drug, subtracting these numbers from the two-day iron clearance after the administration of the drug, and then dividing by the theoretical output; the result is expressed as a percent.

Example 3

This example compares the effectiveness in *Cebus apella* monkeys of subcutaneously administered mono-sodium salt of HBED (MS HBED) in accordance with the invention vs. orally administered HBED monohydrochloride monohydrate and subcutaneously administered DFOM. The comparators include the timeline of iron excretion induced by the iron chelators and the peak amounts of iron excreted.

Chelator-induced iron excretion in *Cebus apella* monkeys

The studies were conducted with *Cebus apella* monkeys to which had been previously administered intravenous iron dextran to provide about 500 mg iron per Kg body weight, as described above. Groups of monkeys (n=6 in each group) were given s.c. injections of either DFOM or MS HBED. DFOM in aqueous solution was given s.c. at a dose of 150 μmoles/Kg and induced the excretion of 435±115 μg Fe/Kg body weight and was found to have an efficiency of 5.1±1.3% (range, 3.3 to 6.6%), with about 65% of the chelator-induced iron excretion in the stool and about 35% in the urine. In our initial experiments, HBED monohydrochloride monohydrate was dissolved in a phosphate buffer at p.7.2 to form a solution of the MS HBED and administered in 40% wt./vol. Cremophor RH-40, a polyethoxylated castor oil used as a vehicle for compounds with poor aqueous solubility, because of the low water solubility of the HBED monohydrochloride monohydrate. HBED monohydrochloride monohydrate-Cremophor was administered by s.c. injection at doses of 75 or 150 μmoles/Kg. At the dose of 75 μmoles/Kg, HBED-Cremophor induced the clearance of 793±410 μ, mg/Kg of iron and had an efficiency of 18.4±9.1% (range, 7.4 to 27.8%). Most of the iron (92%) was excreted in the feces, while 8% excreted in the urine. At a dose of 150 μmoles/Kg, HBED-Cremophor induced the clearance of 1349±475 μg/Kg, an efficiency of 16.1 i 5.6% (range, 9.3 to 23.0%). Once again, the majority of the iron, 90%, was excreted in the feces; 10% was found in the urine.

In order to mimic potential clinical applications, MS HBED was given s.c. to the same group of monkeys used in the preceding experiments at a dose of 150 μmoles/Kg in a phosphate buffer; no Cremophor vehicle was used. Once again, subcutaneous MS HBED induced the excretion of about twice as much iron as DFOM, 899±193 μg Fe/Kg body weight (P<0.001), and was found to have an efficiency of 10.7±2.3% (range, 8.3 to 13.8%), with about 92% of the chelator-induced iron excretion in the stool and about 8% in the urine. At the dose of 150 μmoles/Kg no significant difference (P>0.2) was found between the mean net iron excretion induced by MS HBED prepared in phosphate buffer or by HBED monohydrochloride monohydrate in Cremophor. The mean iron excretion induced by DFOM given s.c. in an aqueous solution and MS HBED administered s.c. in a buffer at a dose of 150 μmoles/Kg body weight are expressed as the mean net amount of iron excreted in the urine and in the feces (μg Fe/Kg body weight) and as the efficiency of iron chelation. The results of this study can be compared to the results of a previously published study of the oral administration of a HBED composition as in a phosphate buffer to a group of *Cebus apella* monkeys with a similar magnitude of iron overload. Oral HBED induced the excretion of only 50±44 μg Fe/Kg body weight and was found to have an efficiency of 0.5±0.5% (range, 0.1 to 1.1%), with about 56% of the chelator-induced iron excretion in the stool and about 44% in the urine. No adverse effects of chelator administration were noted in the monkeys; all hematological and biochemical tests remained within normal ranges.

Example 4

This example explains how to make a mono-cationic salt of HBED. The formula numbers (1)–(5) may be found under the "novel compounds" section of the specification.

A. Mono-sodium HBED (1) Ethylenediamine (MW=60.1, d=0.899) (475 g, 528 ml, 7.91 moles) was added at a rapid dropwise rate from a constant pressure addition funnel to a solution of salicylaldehyde (MW=122.12, d=1.146) (1.93 Kg, 1.68 liter (L.), 15.8 moles, 2.0 equiv.) over 1.15 hr. The exothermic reaction was kept below reflux using a water bath periodically. During the addition, another 300 ml of EtOH was added to facilitate stirring, which was continued overnight. The reaction mixture was cooled for 1 h in an ice bath and filtered to give yellow iridescent flakes and a brown solution. The solid product was washed with EtOH (1.2 L.) and air dried to produce 2314 g of a compound of formula 1 (bf quantitive yield) (MW-268.32).

(2) To a stirred solution of the compound of formula (1) (2122 g, 7.91 moles) in 7 L. of EtOH (SD 3) and 17 L. of THF was added $NaBH_4$, (628 g, 16.6 moles, 2.1 equiv in 50 g portions). The addition required 6 hr. The reaction was allowed to continue overnight and then concentrated in vacuo to remove the solvents, the residue was dissolved in dichloromethane (DCM:17 L.), washed with water (3 L.), dried over $NIC_2SO_4$, and then filtered. Concentration in vacuo to approximately 4 L gave a heterogeneous mixture which was filtered and the resulting solid was washed with 1:1 DCM:Hexane. It was washed with another 2 L. of hot DCM. Hexane (2 L.) was added to the DCM, and a precipitate formed that was filtered off. Hexane (6 L.) was added to the mixture and a precipitate formed. The DCM/hexane mixtures were filtered, and all the resulting filtered solids dried to give 876 g (41%, 3.22 moles) of a white solid identified as formula 2, TL (9:1:0.3 DCM:MeOH:$NEt_3$) one spot, mp 122–125 ° C.

(3) Potassium carbonate (691 g, 5.0 moles, 3.0 equiv.) was added to a stirred solution of the compound of formula (2) (450 g, 1.64 moles) in DMSO (1.9 L). The mixture was cooled to 12°–14° C. using a water bath, and tert-butyl bromoacetate (683 g, 3.50 moles, 2.1 equiv.) was added over 30 min. After 2 days at room temperature, the reaction was poured into DCM (1.5 L). This was filtered and washed with water (7×1.5 L.), dried ($Na_2SO_4$), and filtered. The DCM was removed in vacuo to give a white foam. This was dissolved in warm (45° C.) benzene (375 m). The solution was added to hexane (2.5 L.) with efficient stirring. After 15–20 min., a precipitate formed. The solution was cooled in an ice bath for 2 hrs. The product was filtered, washed with hexane, air dried, and then dried in vacuo under high vacuum at 30–35° C. to give 450 g of a white solid identified as formula 3 (0.9 moles, 54%) mp =80–81° C.

(4) Cold formic acid (1 L.) was added to the compound of formula 3 (450 g, 0.9 moles). After stirring at room temperature for 5 days, the reaction mixture was poured into diethyl ether (4 L.) while swirling to give 2 layers. The top layer was decanted and discarded. The lower layer was poured into stirred diethyl ether (3 L.), giving a white solid. The liquid phase was decanted, and the remaining solid was dissolved in absolute EtOH (absolute, 1.5 L., no heat). This was poured into stirred diethyl ether (2.5 L.) to again give a white solid and clear solution. After decanting the liquid, the solid was dissolved in absolute EtOH (1.6 L., no heat) and stirred overnight. The solution poured into stirred diethyl ether (3.5 L.). The resulting solid was filtered, washed with ether, then quickly transferred to a flask, and toluene (0.5 L.) was added. This was removed in vacuo at 25° C. The white solid was dried overnight in a vacuum oven at 25° C. to give 145 g of a white solid. This solid was treated with acetonitrile (1.4 L.) while being stirred, then water (140 mL) was added. The resulting heterogeneous mixture was stirred for 1 hr. and then filtered. The solid was washed with acetonitrile then DCM, giving 105 g of HBED after drying at 25° C. under high vacuum overnight. A portion of this material (94 g) this was treated with absolute EtOH (450 mL) and stirred for 4 h. It was filtered, washed with more EtOH (150 mL) and then dried overnight under high vacuum at 25° C., giving 89.5 g (0.23 moles, 26% yield) of HBED, shown as formula 4.

(5) HBED (89 g, 0.23 moles) was placed into a 1 L. Erlenmeyer flask with a magnetic stir bar, and water (J T Baker, cat #4218-03,100 ml) was added. This heterogeneous solution was stirred and cooled in an ice bath for 10 min., then a solution of NaOH in water (13.29 g, 0.23 moles (prepared from Alfa Aesar cat #41281 and J T Baker water, 340 mL) was added dropwise over 30 min. After the addition was finished, pH =7.2. A precipitate began to form, which redissolved upon addition of more water (100 mL). Filtration through 0.45 micron filters (Whatman, PTFE), concentration of the filtrate in vacuo at 25–30° C., and further drying under high vacuum at room temperature for 2.5 days gave (91 g) white solid, confirmed to be HBED, monosodium salt, the compound of formula 5 where M is Na.

B. Other mono-cationic salts of HBED.

By following the procedure of part A of this example but substituting other bases for NaOH in step (5), other salts are obtained, such as:

mono-ammonium HBED, mono-potassium HBED, mono-lithium HBED, and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of treating a primate having a condition that is treatable by an iron chelator, which method comprises subcutaneously administrating a therapeutically effective amount of a mono-cationic salt of N,N'-bis(2-hydroxybenzyl)ethylenediamine-N,N'-diacetic acid.

2. The method of claim 1, wherein the condition is iron overload.

3. The method of claim 2, wherein the condition is primary hemochromatosis.

4. The method of claim 2, wherein the condition is secondary hemochromatosis.

5. The method of claim 2, wherein the iron overload is transfusional overload.

6. The method of claim 5, wherein the transfusional overload occurs in a human with sickle cell anemia.

7. The method of claim 5, wherein the transfusional overload occurs in a human with thalassemia major.

8. The method of claim 1, wherein the mono-cationic salt is a mono-sodium salt.

9. The method of claim 1, wherein the mono-cationic salt is a mono-ammonium salt.

10. The method of claim 1, wherein the mono-cationic salt is combined with a pharmaceutically-acceptable excipient as an injectable aqueous solution.

11. A pharmaceutical composition comprising a pharmaceutically-acceptable excipient suitable for subcutaneous injection in combination with a mono-cationic salt of N,N'-bis (2-hydroxybenzyl)ethylenediamine-N,N'-diacetic acid.

12. The composition of claim 11, wherein the mono-cationic salt is the mono-sodium salt.

13. The composition of claim 11, wherein the mono-cationic salt is the mono-ammonium salt.

14. The composition of claim 11, wherein the salt is combined with a pharmaceutically-acceptable excipient as an injectable solution.

15. The composition of claim 14, wherein the salt is combined with a pharmaceutically-acceptable excipient as an aqueous solution.

16. The composition of claim 11 wherein the composition is in the form of a dry material for reconstitution with a liquid carrier.

17. The composition of claim 16 wherein the liquid carrier is a solvent for the dry material.

18. The composition of claim 16 wherein the composition includes a liquid component and the liquid component is miscible with liquid carrier.

19. An article of manufacture that comprises a container containing a pharmaceutical composition comprising a mono-cationic salt of N,N'-bis(2-hydroxybenzyl)ethylenediamine-N,N'-diacetic acid, wherein the container is associated with printed labelling instructions for subcutaneous administration of the composition to treat a condition in a primate that is treatable by an iron chelator.

20. The article of manufacture of claim 19, wherein the condition is iron overload.

21. The article of manufacture of claim 20, wherein the condition is primary hemochromatosis.

22. The article of manufacture of claim 20, wherein the condition is secondary hemochromatosis.

23. The article of manufacture of claim 20 wherein the iron overload is transfusional overload.

24. The article of manufacture of claim 23, wherein the transfusional overload occurs in a human having sickle cell anemia.

25. The article of manufacture of claim 23, wherein the transfusional overload occurs in a human having thalassemia major.

26. The article of manufacture of claim 19, wherein the monocationic salt is the mono-sodium salt.

27. The article of manufacture of claim 19, wherein the mono-cationic salt is the mono-ammonium salt.

28. The article of manufacture of claim 19, wherein the mono-cationic salt is combined with a pharmaceutically-acceptable excipient as an injectable solution.

29. The article of manufacture of claim 28, wherein the mono-cationic salt is combined with a pharmaceutically-acceptable excipient as an aqueous solution.

30. A process for preparing a pharmaceutical composition, which process comprises combining a pharmaceutically-acceptable excipient suitable for subcutaneous injection with a mono-cationic salt of N,N'-bis(2-hydroxybenzyl)ethylenediamine-N,N'-diacetic acid.

31. The process of claim 30, wherein the mono-cationic salt is the mono-sodium salt.

32. The process of claim 30, wherein the mono-cationic salt is the mono-ammonium salt.

33. The process of claim 30, wherein the monocationic salt is combined with a pharmaceutically-acceptable excipient as an injectable solution.

34. The process of claim 33, wherein the mono-cationic salt is combined with a pharmaceutically-acceptable excipient as an aqueous solution.

35. A compound that is a mono-cationic salt of N, N'-bis (2-hydroxybenzyl) ethylenediamine-N, N'-diacetic acid.

36. The compound of claim 35 wherein said cation is selected from pharmaceutically acceptable mono-valent inorganic cations.

37. The compound of claim 36 wherein said monovalent inorganic cation is an alkali metal cation.

38. The compound of claim 35, wherein the salt is the mono-sodium salt.

39. The compound of claim 35, wherein the salt is the mono-ammonium salt.

\* \* \* \* \*